United States Patent
Wirth et al.

(10) Patent No.: US 6,384,082 B1
(45) Date of Patent: May 7, 2002

(54) SNAIL BAIT

(75) Inventors: Wolfgang Wirth, Bergisch Gladbach; Hans-Jürgen Schnorbach, Monheim, both of (DE)

(73) Assignee: Bayer Akitengesellschaft, Leverkusen (DE)

(*) Notice: Subject to any disclaimer, the term of this patent is extended or adjusted under 35 U.S.C. 154(b) by 0 days.

(21) Appl. No.: 09/763,649

(22) PCT Filed: Aug. 18, 1999

(86) PCT No.: PCT/EP99/06045
§ 371 Date: Feb. 26, 2001
§ 102(e) Date: Feb. 26, 2001

(87) PCT Pub. No.: WO00/11948
PCT Pub. Date: Mar. 9, 2000

(30) Foreign Application Priority Data

Aug. 29, 1998 (DE) .......................... 198 39 480

(51) Int. Cl.⁷ ............................ A61K 31/135
(52) U.S. Cl. ............................ 514/646
(58) Field of Search .......................... 514/646

(56) References Cited

FOREIGN PATENT DOCUMENTS

| | | |
|---|---|---|
| CH | 296 097 | 6/1950 |
| DE | 3503608 | 8/1986 |
| DE | 3612161 | 10/1987 |
| DE | 4111389 | 10/1992 |
| EP | 0 045 280 | 2/1982 |
| EP | 384251 * | 8/1990 |
| EP | 0 384 251 | 9/1990 |
| FR | 2050908 | 4/1971 |
| WO | 96/05728 | 2/1996 |

* cited by examiner

Primary Examiner—Alton Pryor
(74) Attorney, Agent, or Firm—Joseph C. Gil

(57) ABSTRACT

Novel slug and snail baits, comprising
 a) 3,5-dimethyl-4-methylthio-phenyl methylcarbamate, optionally in a mixture with one or more other molluscicidally active compounds,
 b) fine cereal flour,
 c) modified starch and a formaldehyde-releasing substance,
 d) molasses and
 e) optionally additives,
a process for preparing these slug and snail baits and their use for controlling terrestrial slugs and snails.

17 Claims, 4 Drawing Sheets

SNAIL BAIT

This application is a 371 of PCT/EP99/06045, filed Aug. 18, 1999.

FIELD OF THE INVENTION

The present invention relates to novel slug and snail baits, to a process for their preparation and to their use for controlling slugs and snails.

BACKGROUND OF THE INVENTION

It is already known to control terrestrial slugs and snails using baits which comprise feedstuffs and molluscicidally active compounds, such as methiocarb, metaldehyde or metal chelates (cf. DE-A 35 03 608, DE 36 12 161 and WO 96-05 728).

Such slug and snail baits can be prepared, for example, by pressing one or more molluscicidally active compounds with feedstuff, carrier material, adhesives and other customary additives essentially dry into shaped articles. These baits have the disadvantage that they have a relatively rough surface, which causes undesirable abrasion during packaging, during transport and also during application. Moreover, it is unfavourable that these shaped articles are relatively unstable under the influence of rainwater, losing some of their activity owing to the beginning decomposition.

Furthermore, it is already known that slug and snail baits based on metaldehyde can be prepared by mixing the active component with the other constituents, but without adhesive, followed, after addition of water, by extrusion and processing into pellets. The activity of these shaped articles is good, but the physical properties under practice conditions are not always sufficient.

SUMMARY OF THE INVENTION

A slug and snail bait includes 3,5-dimethyl-4-methylthio-phenyl methylcarbamate, fine cereal flour, modified starch, a formaldehyde-releasing substance, and molasses.

DETAILED DESCRIPTION

This invention, accordingly, provides novel slug and snail baits, comprising
  a) 3,5-dimethyl-4-methylthio-phenyl methylcarbamate of the formula,

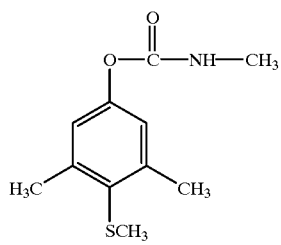

(I)

optionally in a mixture with one or more other molluscicidally active compounds,
  b) fine cereal flour,
  c) modified starch and a formaldehyde-releasing substance,
  d) molasses and
  e) optionally additives.

Furthermore, it has been found that the novel slug and snail baits can be obtained when
  (1) 3,5-dimethyl-4-methylthio-phenyl methylcarbamate of the formula,

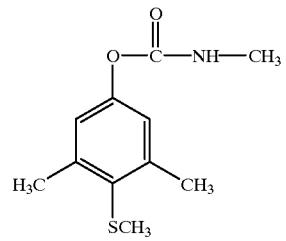

(I)

optionally in a mixture with one or more other molluscicidally active compounds,
  and optionally in a mixture with additives, is mixed and finely ground,
  (2) the resulting premix is mixed with
  fine cereal flour,
  modified starch and a formaldehyde-releasing substance and then sprayed with molasses,
  (3) the resulting homogeneous mixture is admixed with sufficient water to form a dough,
  (4) the dough is extruded and comminuted and
  (5) the resulting product is dried.

Finally, it has been found that the novel slug and snail baits are highly suitable for controlling terrestrial slugs and snails.

It is extremely surprising that the slug and snail baits according to the invention have a better stability than the prior-art shaped articles for the same intended use. It is particularly unexpected that the baits according to the invention, in spite of containing a relatively small amount of adhesive, are, in particular with respect to rain water, considerably more stable than corresponding baits prepared by dry pressing which contain a considerably higher quantity of adhesive.

The slug and snail baits according to the invention have a number of advantages. Thus, they have high abrasion resistance. It is furthermore favourable that they maintain their shape and activity even after prolonged watering.

The slug and snail baits according to the invention are characterized by the constituents listed under (a) to (e).

The molluscicidally active compound that is contained in the baits according to the invention is in each case 3,5-dimethyl-4-methylthio-phenyl methylcarbamate of the formula (I), which is known under the common name methiocarb.

Other molluscidically active compounds which may additionally be present are preferably metaldehyde and metal chelates, such as complexes of ethylenediamine-tetraacetic acid and iron or copper ions.

The cereal flours that may be contained in the slug and snail baits according to the invention are commercial flours, such as wheat flour, rye flour, rice starch, inter alia. Preference is given to durum wheat flour and wheat flour. The flour is present in a fine form, preferably in particle sizes below 250μ.

In the present case, modified starch is to be understood as meaning commercial products of this type. Preference is given to cold-swelling maize starch.

As formaldehyde-releasing substances, the baits may comprise all customary products which are suitable for releasing formaldehyde. Preference is given to urea/formaldehyde condensates.

In the present case, molasses are to be understood as customary syrup-like mother liquors obtained in the manufacture of sugar.

Suitable additives which may be contained in the baits according to the invention are preferably preservatives, colorants, slug and snail attractants, grinding auxiliaries, bitter substances, homeotherm repellents and anticaking agents, and also water.

Examples of preservatives which may be mentioned are 2-hydroxybiphenyl, sorbic acid, p-hydroxy-benzaldehyde, methyl p-hydroxy-benzoate, benzaldehyde, benzoic acid, propyl p-hydroxy-benzoate and p-nitro phenol.

Examples of colorants which may be mentioned are inorganic pigments, iron oxide, titanium dioxide and Prussian Blue, and also organic dyes, such as anthraquinone, azo and metal phthalocyanine dyes.

Suitable slug and snail attractants are all customary substances suitable for this purpose. Examples which may be mentioned are plant extracts and derivatives thereof, and products of animal origin.

Suitable grinding auxiliaries are all substances which can customarily be used for this purpose. Kaolins, aluminas, talc, chalk, quartz powder and finely divided silica may be mentioned as being preferred.

Suitable homeotherm repellents which have a repellent effect on warm-blooded organisms, such as dogs or hedgehogs, are all components which are customary for this purpose. The example which may be mentioned is nonyloic acid vanillamide.

Suitable bitter substances are all substances which are customary for this purpose. An example which may be mentioned is denatonium benzoate.

Suitable anticaking agents are all substances which are customary for this purpose and which prevent lumping and caking. Examples which may be mentioned are moisture-adsorbing powders of kieselguhr, pyrogenic silica, tricalcium phosphate, calcium silicates, aluminium oxide, magnesium oxide, magnesium carbonate, zinc oxide, stearates and fatty amines.

The content of the individual components in the slug and snail baits according to the invention can be varied within a certain range. Thus, the concentrations of active compound of the formula (I), optionally in a mixture with one or more other molluscicidally active compounds, are generally between 0.5 and 15% by weight, preferably between 1.0 and 13% by weight, of cereal flour are generally between 60 and 90% by weight, preferably between 65 and 85% by weight, of modified starch and formaldehyde-releasing substance are generally between 0.1 and 6% by weight, preferably between 0.2 and 5% by weight, of molasses are generally between 1 and 10% by weight, preferably between 2 and 4% by weight, and of additives are generally between 0 and 5% by weight, preferably between 0 and 3% by weight.

When carrying out the process according to the invention, preference is given to using those components which have already been mentioned as being preferred in connection with the description of the slug and snail baits according to the invention for the constituents listed under (a) to (e).

The quantities of the individual components are chosen such that the substances are present in the slug and snail baits according to the invention in the weight ratios mentioned above. However, the amount of water is such that a dough is formed in Step (3) of the process. In general, the amount of water used is between 25 and 35% by weight, preferably between 27 and 34% by weight, based on the other constituents. However, in the slug and snail baits according to the invention, the water content is considerably lower, since the product, which is initially obtained in moist form, is then dried in Step (5) of the preparation process. What remains is virtually only the residual moisture present in the cereal flour.

When carrying out the process according to the invention, the temperatures can be varied within a certain range.

Step (1) is generally carried out at temperatures between 0° C. and 30° C., preferably at room temperature, Step (2) is generally carried out at temperatures between 0° C. and 30° C., preferably at room temperature, Step (3) is generally carried out at temperatures between 0° C. and 40° C, preferably between 10° C. and 30° C., Step (4) is generally carried out at temperatures between 20° C. and 60° C., preferably between 30° C. and 50° C. and Step (5) is generally carried out at temperatures between 20° C. and 90° C., preferably between 30° C. and 80° C.

Steps (1) to (3) and (5) of the process according to the invention are generally carried out under atmospheric pressure. However, it is also possible to carry out the drying process in Step (5) under reduced pressure. Step (4) is generally carried out under elevated pressure, preferably under a pressure between 30 and 100 bar.

All equipment which is customarily used for such processes can be employed for carrying out the process according to the invention. Thus, for comminuting the material in Step (1), customary grinding equipment, such as, for example, airjet mills, are used.

Suitable mixers for the mixing processes in Steps (2) and (3) are customary mixers into which additional substances, such as molasses and water, can be injected during the mixing process. Preference is given to using ploughshare mixers, paddle mixers and twin-screw extruders.

Suitable for the extrusion in Step (4) is the equipment which is customary in the food industry and which can be used to extrude a dough through perforated discs and then to comminute the extrudate.

Suitable for drying the moist product in Step (5) are customary apparatuses which are suitable for removing moisture from particulate solid substances. In a preferred embodiment, the moist product is initially predried in a fluidized bed and then dried to the desired final moisture in a separate piece of equipment.

Specifically, the process according to the invention is carried out by mixing, in Step (1), the active compound of the formula (I), optionally in a mixture with one or more other molluscicidally active compounds and optionally with additives, such as, for example, grinding auxiliaries, preservatives, colorants, and the like, and finely grinding the resulting mixture, mixing, in Step (2), the resulting premix with fine cereal flour, modified starch and formaldehyde-releasing substance, then adding molasses in liquid form and mixing the components to a homogeneous product, adding, in Step (3), a sufficient quantity of water with mixing and kneading, so that a dough is formed, extruding under pressure and comminuting, in Step (4), the dough and initially predrying and then drying, in Step (5), the particulate material, followed by cooling to room temperature.

When carrying out the process according to the invention, the size of the slug and snail baits can be varied within a certain range in the particular desired manner. In general, the dough is comminuted such that pellets or strand-shaped particles are formed. The average diameter or the average length of the particles is generally between 1 and 4 mm, preferably between 1.5 and 3 mm.

The slug and snail baits according to the invention are highly suitable for controlling terrestrial slugs and snails in agriculture and horticulture. The slugs and snails include all terrestrial slugs and snails, most of which occur as polyphagous pests in agricultural and horticultural crops. Important pests of these types are slugs, such as *Arion rufus* (red slug), *Arion ater* and other Arionidae, Limax species, furthermore field slugs, such as *Deroceras reticulatum* and *Deroceras agreste* from the family Limacidae, and species from the family Milacidae, and moreover harmful snails, such as those from the genera Cepaea, Discus, Helicigona and Helicella.

In the control of slugs and snails, the application rate of the baits according to the invention can be varied within a wide range. In general, between 2 and 15 kg of slug and snail bait are used per hectare, preferably between 3 and 7 kg per hectare.

The slug and snail baits according to the invention can be applied by customary methods, such as, for example, by scattering and drilling.

The invention is illustrated by the examples below.

EXAMPLE 1

Preparation of slug and snail bait according to the invention.

Figure 1:
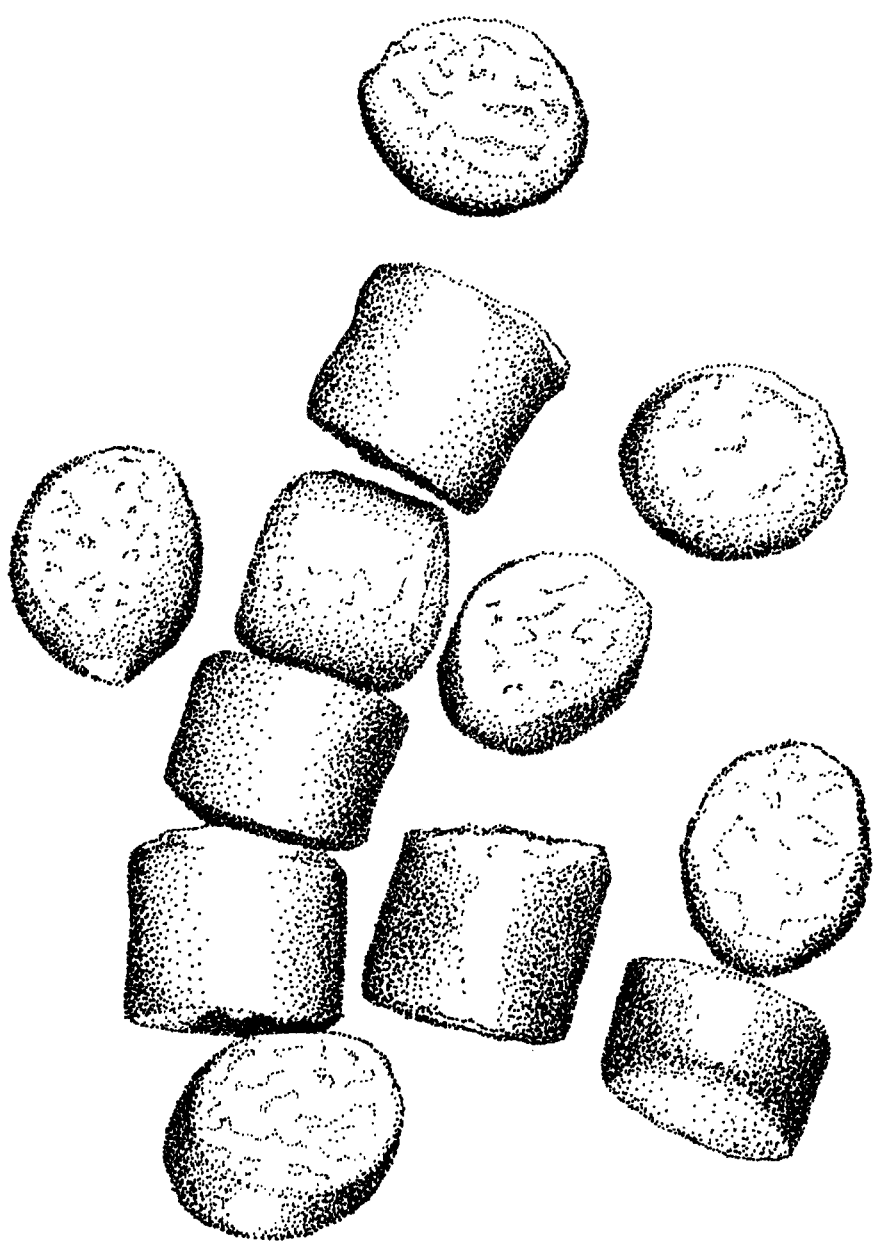
FIGS. 1–4: Slug and snail bait in the form of pellets.

A mixture of 400 g of 3,5-dimethyl-4-methylthio-phenyl methylcarbamate, 15 g of p-nitrophenol, 29 g of blue colour pigment and 56 g of finely divided silica is finely ground at room temperature. The resulting premix is mixed in a mixer with 8500 g of wheat flour of a particle size of less than $250\mu$, 250 g of cold-swelling maize starch and 50 g of urealformaldehyde condensate, with stirring at room temperature. With further stirring, 700 g of liquid molasses are then sprayed on at room temperature. At room temperature, the resulting mixture is mixed with 3000 g of water and mixed and kneaded until a homogeneous dough has formed. The dough is then, at 40° C. and under a pressure of 60 bar, extruded in the form of strands through a perforated disc, and the strands are comminuted into segments of a length of 2 to 3 mm. The resulting material is initially dried in a fluidized bed at temperatures between 30° C. and 80° C. and then in a separate drier at temperatures between 30° C. and 80° C. This gives 10,000 g of slug and snail bait in the form of pellets, which are shown in enlarged form in FIG. 1.

It is noticeable that the particles have a relatively smooth surface.

Comparative Example

Preparation of known slug and snail bait.

Figure 2:
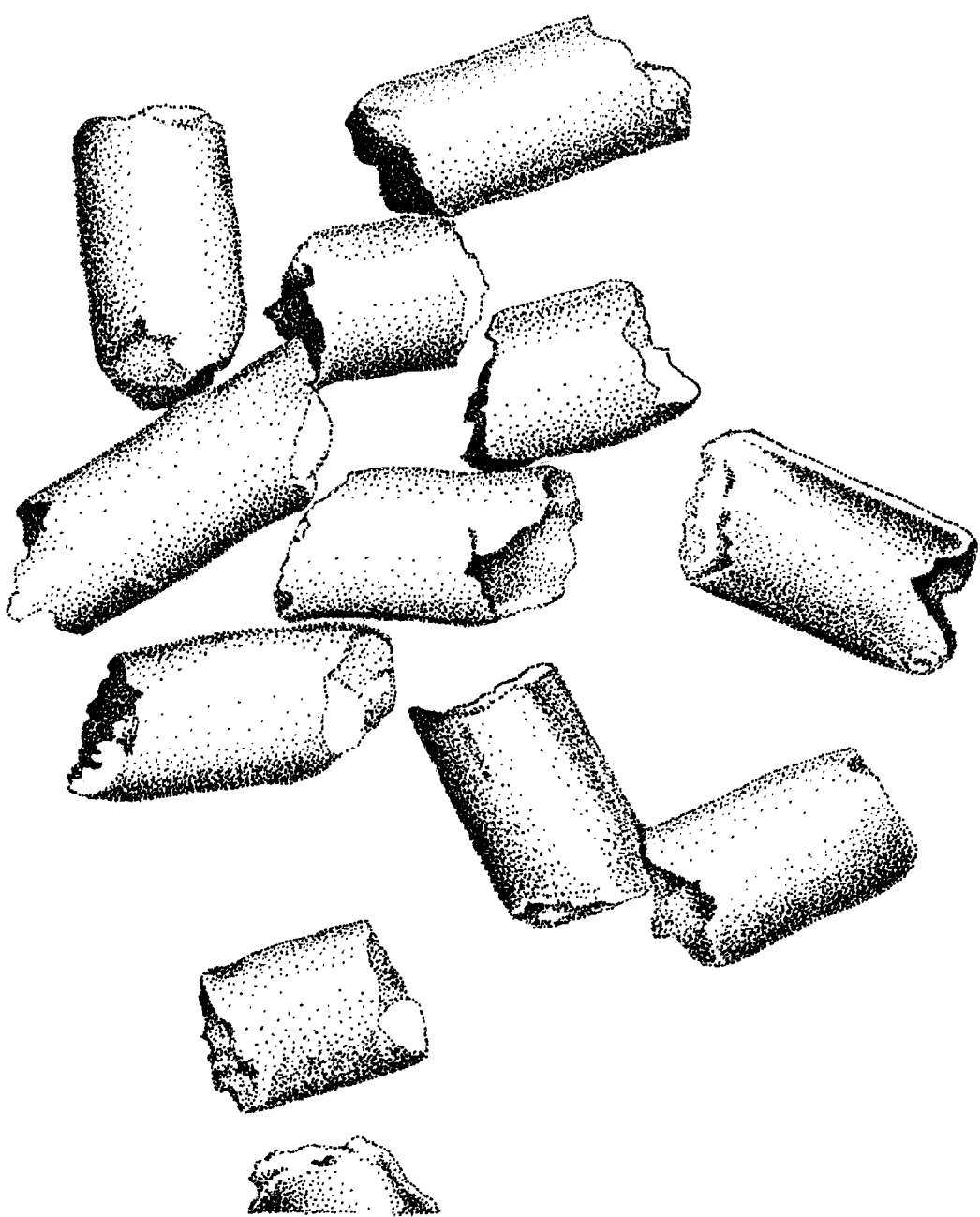

A mixture of 400 g of 3,5-dimethyl-4-methylthio-phenyl methylcarbamate, 15 g of p-nitrophenol, 29 g of blue colour pigment and 56 g of finely divided silica is finely ground at room temperature. The resulting premix is mixed in a mixer with 7600 g of coarse wheat meal of a particle size of about $500\mu$ and 1200 g of binder with stirring at room temperature. With further stirring, 700 g of liquid molasses are then sprayed on at room temperature. At a temperature of 60° C., the resulting mixture is extruded under pressure through an annular die to give elongated particles having an average length of 2 to 3 mm. In this manner, 10,000 g of slug and snail bait in the form of elongated particles are obtained, an enlarged picture of which is shown in FIG. 2. It is noticeable that the particles have rough broken edges.

Stability Test

In a glass dish, in each case 0.5 g of slug and snail bait according to Example 1 or 0.5 g of slug and snail bait according to the comparative example is in each case applied over the entire area, covered with in each case 100 ml of water and allowed to stand for 24 hours. The baits are then assessed visually.

Figure 3:
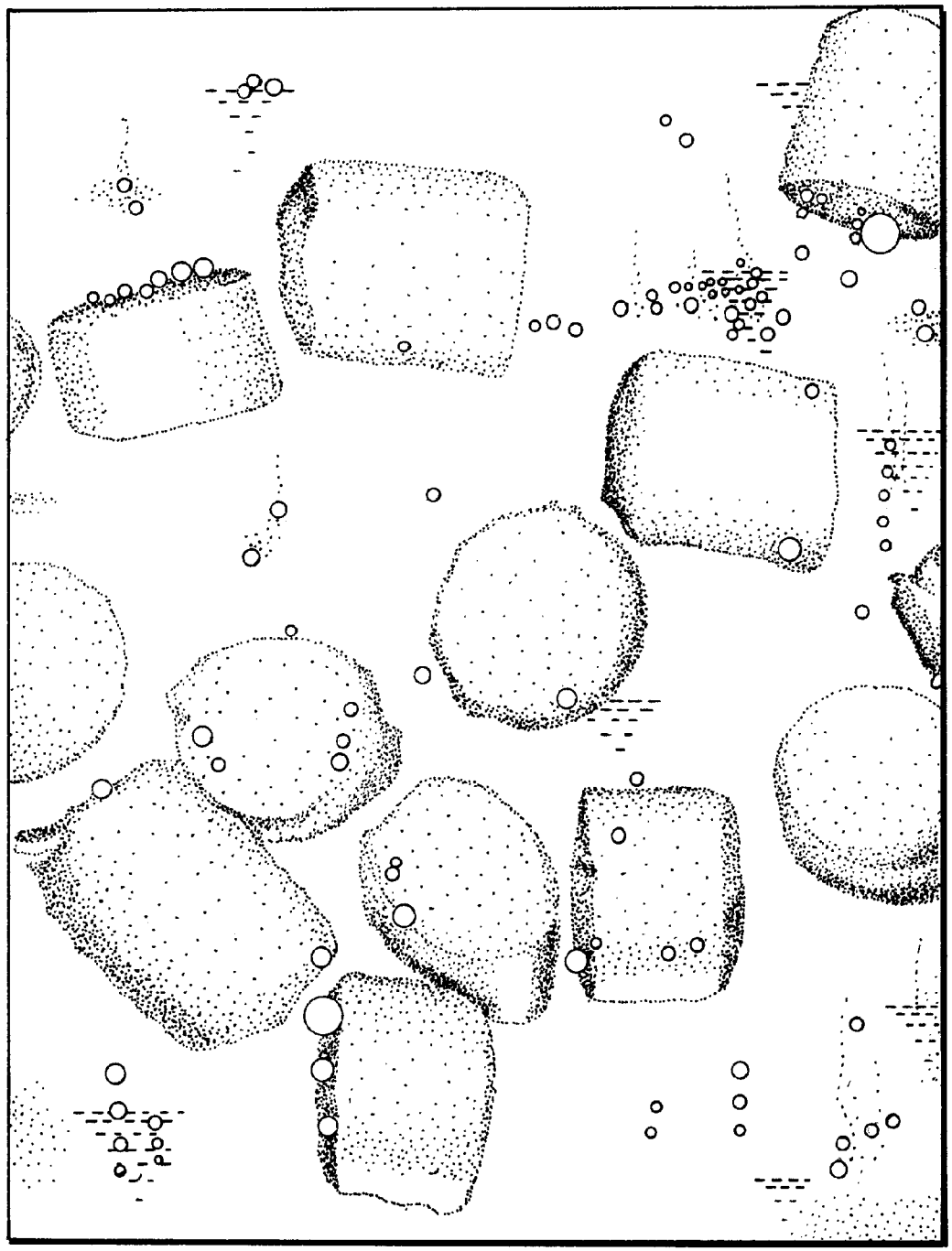

FIG. 3 shows slug and snail baits according to Example 1 after the treatment with water.

Figure 4:
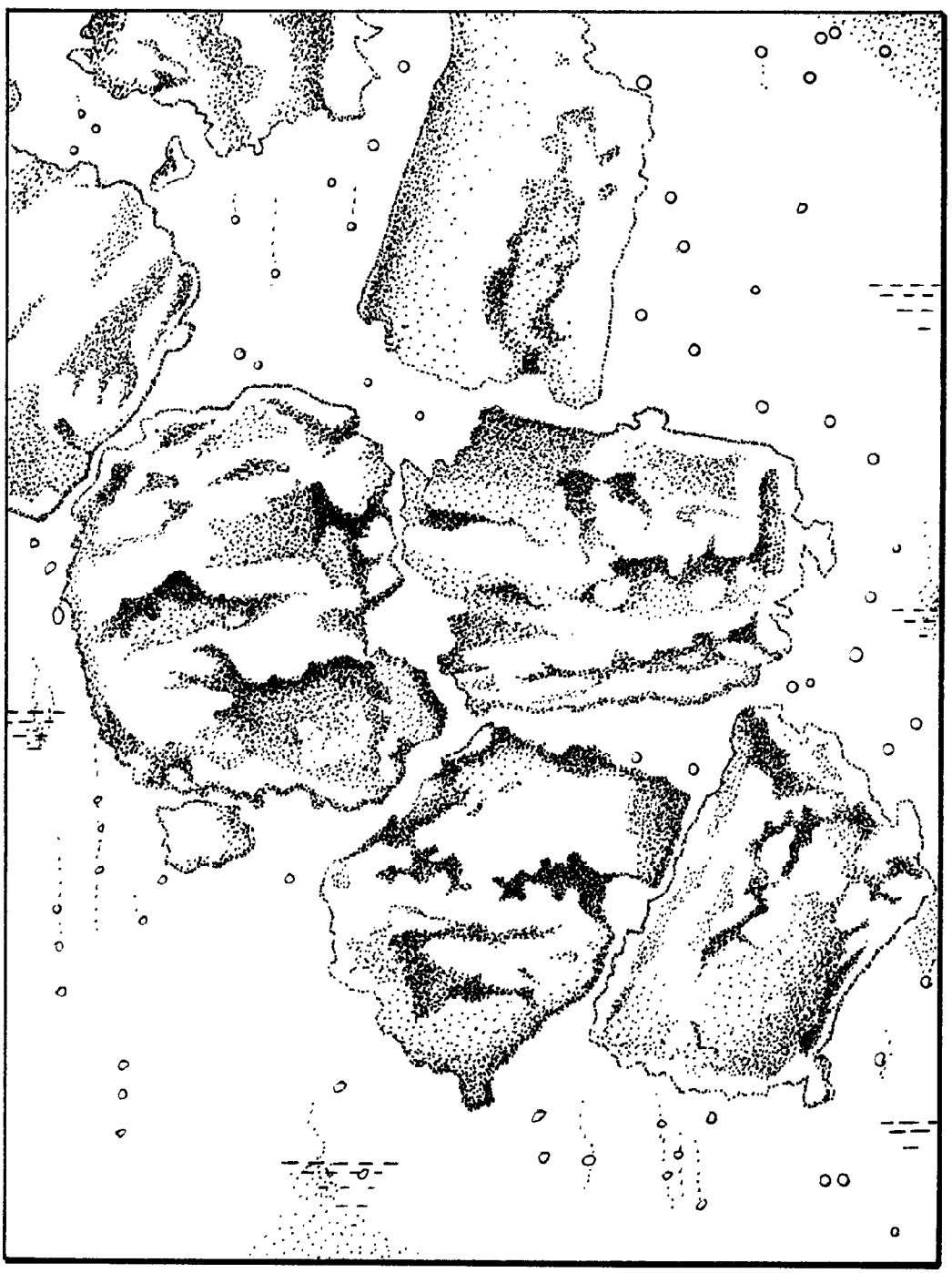

FIG. 4 shows slug and snail baits according to the comparative example after the treatment with water.

It can be seen that the bait material according to the invention is, even after the treatment with water, present in its original form and still virtually intact, whereas most of the bait material according to the comparative example is present in disintegrated form.

What is claimed is:

1. A slug and snail bait, comprising a) 3,5-dimethyl-4-methylthio-phenyl methylcarbamate of the formula,

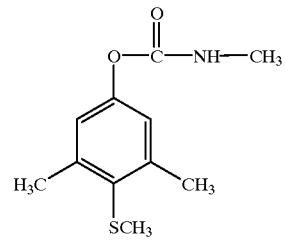

(I)

optionally in a mixture with one or more other molluscicidally active compounds, b) fine wheat or durum wheat flour having a particle size below $250\mu$ c) modified starch and an urea/formaldehyde condensate, d) molasses and e) one or more additives selected from the group consisting of preservatives, colorants, slug and snail attractants, grinding auxiliaries, bitter substances, homeotherm repellents and anticaking agents and water.

2. A process for preparing a slug and snail bait according to claim 1, comprising the steps of
(1) finely grinding a 3,5-dimethyl-4-methylthio-phenyl methylcarbamate of the formula,

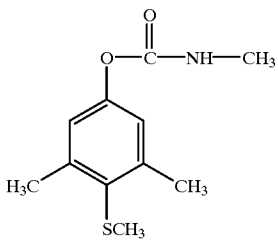

(I)

optionally in a mixture with one or more other molluscicidally active compounds, and in a mixture with additives,
(2) mixing resulting premix with the fine wheat or durum wheat flour having a particle size below 250µ, and said modified starch and an urea/aldehyde condensate and then spraying the premix with molasses,
(3) admixing the resulting homogeneous mixture with sufficient water to form a dough,
(4) extruding and comminuting the dough, and
(5) drying the resulting product.

3. A method for controlling terrestrial slugs and snails, comprising the step of applying a slug and snail bait according to claim 1 to the habitat of the slugs and snails.

4. A slug and snail bait according to claim 1, wherein the slug and snail bait is in the form of particles having an average diameter of between 1 and 4 mm and an average length of between 1 and 4 mm.

5. A slug and snail bait according to claim 1, comprising
a) between 0.5 and 15% by weight of active compound of the formula (I),
b) between 60 and 90% by weight said wheat flour,
c) between 0.1 and 6% by weight of said modified starch and said urea/formaldehyde formaldehyde-condensate,
d) between 1 and 10% by weight of molasses.

6. A slug and snail bait according to claim 5, comprising between 0 and 5% by weight of said additives.

7. A method according to claim 3, wherein the slug and snail bait is applied at a rate of between 2 and 15 kg of bait per hectare.

8. A slug and snail bait comprising:
a) 3,5-dimethyl-4-methylthio-phenyl methylcarbamate,
b) fine cereal flour,
c) modified starch and an urea/formaldehyde condensate,
d) molasses,
e) an additive selected from the group consisting of preservatives, colorants, slug and snail attractants, grinding auxiliaries, bitter substances, homeotherm repellents and anticaking agents, water and mixtures thereof, and
f) a molluscidically active compound selected from complexes of ethylenediamine-tetraacetic acid and iron or copper ions.

9. A slug and snail bait according to claim 8, wherein the fomaldehyde releasing substance is selected from the group consisting of urea/formaldehyde condensates and the modified starch the modified starch is a cold-swelling maize starch.

10. A slug and snail bait comprising:
a) 3,5-dimethyl-4-methylthio-phenyl methylcarbamate,
b) fine cereal flour,
c) modified starch and an urea/formaldehyde condensate,
d) molasses, and
e) an additive selected from the group nonyloic acid vanillamide, denatonium benzoate, 2-hydroxybiphenyl, sorbic acid, p-hydroxy-benzaldehyde, methyl p-hydroxy-benzoate, benzaldehyde, benzoic acid, propyl p-hydroxy-benzoate, p-nitro phenol and mixtures thereof.

11. A method of improving stability of a slug and snail bait to rainwater comprising the steps of:
(1) finely grinding 3,5-dimethyl-4-methylthio-phenyl methylcarbamate to obtain a premix,
(2) mixing the premix with fine cereal flour having a particle size below 250µ, modified starch and an urea/formaldehyde condensate and then adding molasses to obtain a homogeneous mixture,
(3) admixing the resulting homogeneous mixture with sufficient water to form a dough,
(4) extruding and comminuting the dough to obtain a product, and
(5) drying the product.

12. A method according to claim 11, wherein the cereal flour is selected from the group consisting of wheat flour, rye flour, rice starch, and mixtures thereof, the modified starch is a cold-swelling maize starch, and the formaldehyde-releasing substance is selected from the group consisting of urea/formaldehyde condensates.

13. A method according to claim 11, wherein the step of finely grinding 3,5-dimethyl-4-methylthio-phenyl methylcarbamate to obtain said premix occurs in the presence of one or more other molluscicidally active compounds.

14. A method according to claim 11, wherein the step of finely grinding 3,5-dimethyl-4-methylthio-phenyl methylcarbamate to obtain said premix occurs in the presence of one or more additives.

15. A method according to claim 11, wherein the step of admixing the homogeneous mixture with sufficient water to form a dough comprises adding an amount of water between 25% and 35%, by weight of the homogeneous mixture.

16. A method according to claim 11, wherein the dough further comprises an additive selected from the group nonyloic acid vanillamide, denatonium benzoate, 2-hydroxybiphenyl, sorbic acid, p-hydroxy-benzaldehyde, methyl p-hydroxy-benzoate, benzaldehyde, benzoic acid, propyl p-hydroxy-benzoate, p-nitro phenol and mixtures thereof.

17. A method according to claim 11, wherein the dough further comprises a molluscicidally active compound selected from complexes of ethylenediamine-tetraacetic acid and iron or copper ions.

* * * * *